United States Patent [19]

Fuller et al.

[11] Patent Number: 5,030,642
[45] Date of Patent: Jul. 9, 1991

[54] ACYLAMINOALKYLPYRIDINEAMIDES AS INHIBITORS OF METASTASIS

[75] Inventors: George C. Fuller, Gross Point, Mich.; George R. Martin, Bethesda, Md.; Richard A. Mueller, Glencoe, Ill.; Reuven Reich, Silver Spring, Md.

[73] Assignees: G. D. Searle & Co., Chicago, Ill.; The Government of the United States of America, as represented by the Secretary, Department of Health and Human Services, Washington, D.C.

[21] Appl. No.: 279,186

[22] Filed: Dec. 2, 1988

[51] Int. Cl.$^5$ .............................................. A61K 31/44
[52] U.S. Cl. .................................... 514/357; 514/351
[58] Field of Search ................................ 514/351, 357

[56] References Cited

U.S. PATENT DOCUMENTS

| | | | |
|---|---|---|---|
| 4,029,812 | 6/1972 | Wagner et al. | 424/324 |
| 4,076,841 | 2/1978 | Wagner et al. | 424/324 |
| 4,078,084 | 3/1978 | Wagner et al. | 424/324 |
| 4,663,333 | 5/1987 | Mueller et al. | 514/346 |

OTHER PUBLICATIONS

Albini, A., et al., Cancer Research, 47:3239–3245, (1987).
Anderson, et al., The Prostate 12:3–12, (1988).
Black, K. L., et al., Annals of Neurology 19(6):592–595, (1986).
Dano et al., Adv. Cancer Res. 44:139–266, (1985).
Fidler, I. J., et al., Adv. Cancer Res. 28:149–250, (1978).
Honn et al., Biochem. Biophys. Res. Commun. 102:1122, (1981).
Honn, et al., Science 212:1270, (1981).
Hujanen, E. S., et al., Cancer Research 45:3517–3521, (1985).
Liotta, L. A., et al., Am. J. Pathology 117:339–348, (1986).
McCarthy, J. B., et al., Cancer Metastasis Rev. 4:125–152, (1985).
Martin, G. R., et al., Ann. Rev. Cell Biol. 3:57–85, (1987).
Murphy, G., et al., Biochem Biophys Acta 831:49–58, (1985).
Nakajima, M., et al., Cancer Research 47:4869–4876, (1987).
Nardone, et al., J. Surg. Res. 44(4):425–429, (1988).
Reich, R., et al., Cancer Res. 48:3307–3312, (1988).
Terranova, V. P., et al., J. Natl. Cancer Inst. 77:311–316, (1986).
Fischer, S. M., et al., Adv. Prostaglandin, Thromboxane, Leukotriene Res., 12:309, (1983).
Honn et al., Adv. Prostaglandin Thromboxane, Leukotriene Res. 12:313, (1983).

Primary Examiner—Jerome D. Goldberg
Attorney, Agent, or Firm—Mary Jo Kanady; Paul D. Matukaitis

[57] ABSTRACT

The present invention relates to a method of inhibiting tumor metastasis in an aminal by administering to an animal in need of such treatment an acrylaminoalkylpryridineamides represented by the formula

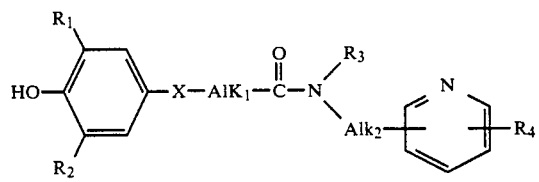

wherein: $R_1$ and $R_2$ are the same or different members of the group consisting of halo, phenyl, substituted phenyl and a

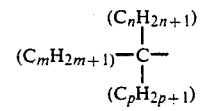

group wherein n, m and p are independently an integer of from 1 to 8 provided $n+m+p$ is equal to or less than 10; x is thio or sulfinyl; $Alk_1$ is straight or branched chain lower alkylene of 1 to 6 carbon atoms, $R_3$ is hydrogen or lower alkyl, $Alk_2$ is straight or branched chain alkylene of 1 to 4 carbon atoms; $R_4$ is selected from the group consisting of hydrogen, halo, hydroxy, lower alkyl and lower alkoxy; or a pharmaceutically acceptable salt thereof, in an amount effective to inhibit tumor metastasis.

9 Claims, No Drawings

ACYLAMINOALKYLPYRIDINEAMIDES AS INHIBITORS OF METASTASIS

The present invention relates to the use of acylaminoalkylpyridineamides and more particularly, acylaminoalkylpyridineamides which are basic, specific 5-lipoxygenase inhibitors to inhibit cell invasive activity and related metastasis in a mammal having tumor cells sensitive to said 5-lipoxygenase inhibitors.

BACKGROUND OF THE INVENTION

It is generally understood that the metastasis of tumor cells is a critical event in the natural history and spread of cancer. The spread of the tumor often places it beyond surgical treatment and results in a drastically worsened prognosis for the patient. Current concepts suggest that metastasis is a complex, multistep process (Fidler, I. J. et. al., *Adv. Cancer Res.*, 28: 149-250, 1978). However, invasion through basement membrane is an essential step in the process by which tumor cells form new lesions and this may involve a common mechanism for many tumor cells. Basement membranes (Martin, G. R., et. al., *Ann. Rev. Cell Biol.*, 3: 57-85, 1987), are the extracellular structures surrounding most epithelial tissues, nerves and muscle and lining most blood and lymph vessels. Collagen IV, laminin and a large heparan sulfate proteoglycan are major components of basement membranes. Basement membranes represent significant barriers to most cells, but malignant tumor cells can penetrate them. This is believed to require degradation by specific proteolytic enzymes (Liotta, L. A., *Am. J. Pathology*, 117: 335-348, 1986), (Terranova, V. P. et. al., *J. Natl. Cancer Inst.*, 77: 311-316, 1986). Because the basement membranes in all tissues have the same components, (Martin, G. R., et. al., *Ann. Rev. Cell Biol.*, 3: 57-85, 1987), it is possible that similar mechanisms are employed by many malignant tumor cells in invading basement membranes, although this has not been shown directly. The degradation of the collagen IV network may be the critical step, (Liotta, L. A., *Am. J. Pathology*, 117: 335-348, 1986), (Terranova, V. P. et. al., *J. Natl. Cancer Inst.*, 77: 311-316, 1986) and it may be possible that collagenase IV is needed to do this. However, this is uncertain since other proteases including gelatinase, stromelysin, and elastase are able to degrade the collagen IV monomer under in vitro conditions (Murphy, G. et. al., *Biochem. Biophys. Acta*, 831: 49-58, 1985).

Collagenase IV is secreted in an inactive form. Activation of the enzyme is achieved via plasminogen activator and plasmin. Inhibition of either enzyme prevents malignant tumor cells from being invasive (Reich, R, et. al., *Cancer Res.* 48: 3307-3312, 1988). A high production of plasminogen activator is frequently observed with malignant cells (Dano, et. al., *Adv. Canc. Res.* 44: 139-266, 1985).

Laminin and the protein of the heparan sulfate proteoglycan are susceptible to a variety of proteolytic enzymes. Degradation of the heparan sulfate chains requires a heparanase, and inhibitors of this enzyme have been shown to be antimetastatic in experimental studies (Nakajima, M., et. al., *Cancer Research*, 47: 4869-4876, 1987).

Motility factors and tissue chemotactic factors can stimulate the movement of malignant tumor cells and have been implicated in the organ specific metastasis of certain tumor cells (Hujanen, E. S. et. al., *Cancer Research*, 45: 3517-3521, 1985). Matrix proteins such as laminin have both chemotactic and heptotactic activity and might be expected to accelerate the movement of malignant tumor cells (McCarthy, J. B. et. al., *Cancer Metastasis Rev.*, 4: 125-152, 1985). In vitro assays of tumor cell invasiveness often employ chemoattractants to increase the migration of the tumor cells (Albini, A. et. al., *Cancer Research*, 47: 3239 3245, 1987). Chemoattractants may have a significant role in tumor cell metastasis.

Hematogenous tumor metastasis is thought to be mediated in part by alterations in vascular integrity and interactions with platlets. Arachidonic acid metabolites, i.e., prostacyclin, thromboxane $A_2$ and leukotrienes are powerful modulators of vascular integrity, tone and platelet aggregation and may be involved in the development of tumor growth and metastasis. There is evidence of a correlation between tissue levels of leukotriene $C_4$ levels and vasogenic edema surrounding brain tumors, K. C. Black, et al. ANNALS OF NEUROLOGY 19(6):592-595 (1986). Honn, et al., demonstrated that selective inhibition of thromboxane synthetase, as well as pretreatment with exogenous prostacyclin significantly decreased hematogenous metastases in animal models. SCIENCE 212:1270(1981); ADV. PROSTAGLANDIN, THROMBOXANE, LEUKOTRIENE RES.12:313 (1983); BIOCHEM. BIOPHYS. RES. COMMUN. 102:1122(1981). Ketoconazole, an antifungal agent which inhibits both the thromboxane synthetase and 5-lipoxygenase metabolic pathways significantly reduce metastasis of B16-F10 murine melanoma cells in mice, P. A. Wardone, et. al, J. SURG. RES. 44 (4): 425-429 (1988). When human PC -3 cells derived from a metastatic prostate adenocarcinoma were incubated with eicosatetraynoic acid, an in vitro inhibitor of arachidonic acid metabolism (cyclooxygenase and lipoxygenase), DNA synthesis was suppressed, K. M. Anderson, et al., THE PROSTATE 12:3-12 (1988).

Cyclooxygenase inhibitors have been used as nonsteroidal antiinflammatory agents (NSAID's) and analgesics. Mixed cyclooxygenase/lipoxygenase inhibitors such as benoxaprofen have been used for the same purposes. Both groups of drugs have exhibited undesirable toxicity in human use (see for example, Goodman and Gilman, *The Pharmacologic Basis of Therapeutics*, Seventh Ed. (1985) Chapter 29 pages 674-715).

Wagner, et al., U.S. Pat. No. 4,029,812, and related U.S. Pat. Nos. 4,076,841 and 4,078,084 which issued from divisional applications of the -812 application, all assigned to The Dow Chemical Company, disclose 2-(3,5-di-tert-butyl-4-hydroxyphenyl) thiocarboxylic acids, esters and simple amides which are hypolipidemics and are useful in reducing plasma lipid levels, especially cholesterol and triglyceride levels.

U.S. Pat. No. 4,663,333 discloses 5-lipoxygenase inhibiting acylaminoalkylpyridines represented by the formula

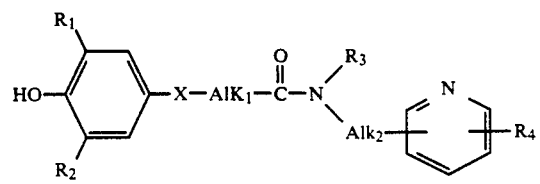

wherein: $R_1$ and $R_2$ are the same or different members of the group consisting of halo, phenyl, substituted phenyl and a

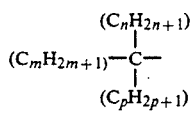

group wherein n, m and p are independently an integer of from 1 to 8 provided n+m+p is equal to or less than 10; X is thio, sulfinyl or sulfonyl; $Alk_1$ is straight or branched chain lower alkylene of 1 to 6 carbon atoms; $R_3$ is lower alkyl; $Alk_2$ is straight or branched chain alkylene of 1 to 4 carbon atoms; $R_4$ is selected from the group consisting of hydrogen, halo, hydroxy, lower alkyl and lower alkoxy; and the pharmaceutically acceptable salts thereof. The compounds specifically block the 5-lipoxygenase pathway of the arachidonic acid cascade and block the formation of the leukotrienes responsible for allergy and inflammation reactions. The compounds are useful in the treatment of allergy and hypersensitivity reactions and inflammation and are particularly useful in the treatment of arthritis and other inflammatory joint disease, asthma, proliferative skin disease such as psoriasis, and the like, alone or in combination with one or more cyclooxygenase inhibitors. There is no disclosure of or suggestion of tumor metastasis inhibiting activity.

SUMMARY OF THE INVENTION

The present invention relates to a method of inhibiting tumor metastasis in an animal by administering to an animal in need of such treatment a therapeutically effective tumor metastasis inhibiting amount of a compound of Formula I

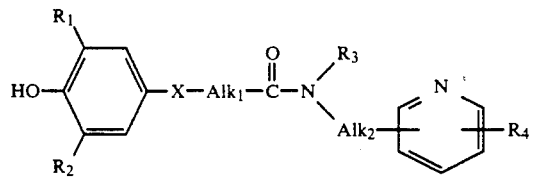

wherein: $R_1$ and $R_2$ are the same or different members of the group consisting of halo, phenyl, substituted phenyl and a

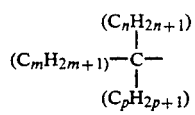

group wherein n, m and p are independently an integer of from 1 to 8 provided n+m+p is equal to or less than 10; X is thio or sulfinyl; $Alk_1$ is straight or branched chain lower alkylene of 1 to 6 carbon atoms, $R_3$ is hydrogen or lower alkyl, $Alk_2$ is straight or branched chain alkylene of 1 to 4 carbon atoms; $R_4$ is selected from the group consisting of hydrogen, halo, hydroxy, lower alkyl and lower alkoxy; and the pharmaceutically acceptable salts thereof.

DETAILED DESCRIPTION OF THE INVENTION

The present invention relates to the use of certain acylaminoalkylpyridineamides to inhibit tumor metastasis in an animal.

In particular the invention relates to a method of inhibiting tumor metastasis in an animal by administering to an animal in need of such treatment a therapeutically effective tumor metastasis inhibiting amount of a compound of the formula

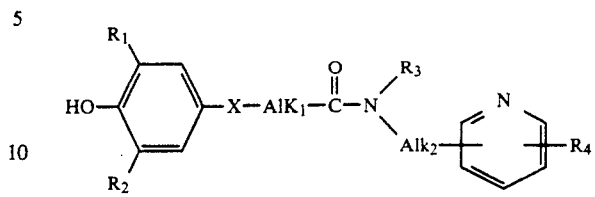

wherein: $R_1$ and $R_2$ are the same or different members of the group consisting of halo, phenyl, substituted phenyl and a

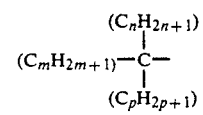

group wherein n, m and p are independently an integer of from 1 to 8 provided n+m+p is equal to or less than 10; X is thio or sulfinyl; $Alk_1$ is straight or branched chain lower alkylene of 1 to 6 carbon atoms, $R_3$ is hydrogen or lower alkyl, $Alk_2$ is straight or branched chain alkylene of 1 to 4 carbon atoms; $R_4$ is selected from the group consisting of hydrogen, halo, hydroxy, lower alkyl and lower alkoxy; and the pharmaceutically acceptable salts thereof.

These compounds are chemically basic, selective 5-lipoxygenase inhibitors which have unexpectedly been found to be useful in inhibiting the metastasis of tumor cells through basement membrane, thereby decreasing the tumor burden. Not all specific 5-lipoxygenase inhibitors are active; for example, acidic compounds were not found to be active in inhibiting tumor metastasis.

The present invention also includes pharmaceutical compositions comprising a tumor metastasis inhibiting effective amount of a compound of formula I in unit dosage form along with a pharmaceutically acceptable carrier.

Preferred compounds for use in inhibiting tumor metastases in an animal in need of such treatment are compounds of the formula

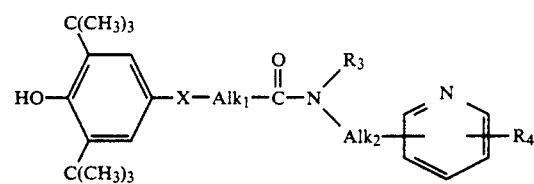

wherein: X is thio or sulfinyl; $Alk_1$ is straight or branched chain lower alkylene of 1 to 6 carbon atoms, $R_3$ is hydrogen or lower alkyl, $Alk_2$ is straight or branched chain alkylene of 1 to 4 carbon atoms; $R_4$ is selected from the group consisting of hydrogen, halo, hydroxy, lower alkyl and lower alkoxy; and the pharmaceutically acceptable salts thereof A particularly preferred compound for use in inhibiting tumor metastasis in an animal in need of such treatment is a compound of the formula

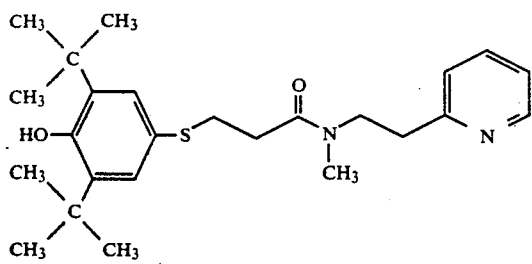

or a pharmaceutically acceptable salt thereof. This compound is active in vivo in inhibiting B16-F10 cell metastasis to the lung in a mouse model.

Generally speaking, synthesis of the compounds used in practicing this invention is accomplished by displacement of the halogen or tosylate on a halo or tosyl substituted aliphatic acyl aminoalkylpyridine or substituted pyridine amide by a thiol in the presence of a base. Addition of a thiol to the double bond of any aliphatic acylaminoalkylpyridine amide is also an effective method of synthesis. Alternatively, the displacement, via reaction with a thiol and base, can be carried out on a tosyl or halo substituted aliphatic carboxylic acid or ester which is then converted into the final product via reaction of the corresponding acid chloride with the desired amine. The sulfones and sulfoxides are readily prepared by oxidation of the sulfides with, for example, m-chloroperbenzoic acid or sodium metaperiodate.

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "lower alkylene", as used herein, refers to straight or branched chain lower alkylene groups having from 1 to 6 carbon atoms, i.e., methylene, ethylene, n-propylene, iso-propylene, n-butylene, sec-butylene, tert-butylene, 3-methylpentylene, 2-methylbutylene, 1,1-dimethylethylene, and the like.

The term "substituted phenyl" refers to phenyl having one or more substituents selected from the group consisting of amino, halo, hydroxy, lower alkyl, lower alkylaminoalkyl, lower dialkylaminoalkyl, trifluoromethyl, lower alkoxy, and the like for $R_4$ and halo, hydroxy, lower alkyl and lower alkoxy for $R_1$ and $R_2$.

The term "halo", as used herein, includes chloro, bromo, iodo and fluoro.

The term "lower alkoxy" refers to alkoxy groups having from 1 to 6 straight or branched chain carbon atoms, i.e., methoxy, propoxy, tert-butoxy, pentoxy etc.

Preferred radicals represented by the group of the formula

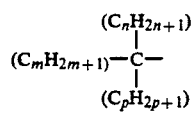

include tertiary alkyl moieties wherein n and m are preferably 1 or 2 and most preferred radical is represented by the group wherein n, m and p are 1, namely t-butyl.

The groups represented by X are preferably thio or sulfinyl and most preferably thio.

The term "pharmaceutically acceptable acid addition salts" refers to physiologically acceptable salts of the compounds of the present invention prepared by treating the compound with an appropriate acid as is well known in the art. Such salts include, but are not limited to, the hydrochloride, hydrobromide, sulfate, maleate, napsylate, oleate, succinate, palmitate, laureate, fumarate, phosphate, acetate, tartrate, stearate, nitrate, citrate, tosylate and like salts.

The metastasis-inhibiting activity of the compounds of this invention was first determined using the assay described in R. Reich, et. al. "Effects of Inhibitors of Plasminogen Activator, Serine Proteases and Collagenase IV on the Invasion of Basement Membranes by Metastatic cells in Mice and Humans," CANCER RESEARCH 48: 3307–3312 (1988) and Albini, A. et. al, "A rapid in vitro assay for quantitating the invasive potential of tumor cells." CANCER RESEARCH 47:3239–3245 (1987).

Chemoinvasion and Chemotaxis Assays. The chemoinvasion assay was performed a previously described by Albini, et. al. Briefly, polyvinylpyrrolidone-free polycarbonate filters, 8-$\mu$m pore size (Nucleopore, Calif.) were coated with an extract of basement membrane components (Matrigel, 25 $\mu$g/filter, i.e., 0.5$\mu$g/mm$^2$) and placed in modified Boyden chambers. This amount of Matrigel forms an even coating over the surface of the filter and the ultrastructure of the reconstituted basement membrane has been reported to resemble, in part, authentic basement membranes. Kleinman, H. K., et. al. "Basement membrane complexes with biological activity," BIOCHEMISTRY, 25: 312–318 (1986). The cells to be studied ($2 \times 10^5$) were collected by short exposure to EDTA (lmM) resuspended in 0.1% bovine serum albumin in Dulbecco's minimum essential medium and placed in the upper compartment of the Boyden chamber. Fibroblast conditioned media were placed in the lower compartment as a source of chemoattractants. The chemotactic assays were conducted in a similar fashion except with a small amount (5$\mu$g/filter) of collagen IV instead of Matrigel. After incubation for 6 h at 37° C. the cells on the lower surface of the filter were stained and quantitated with an image analyzer (Optomax IV) attached to an Olympus CK2 microscope. The data are expressed as the area of the bottom surface of the filter occupied by cells and is proportional to the number of cells on this surface. Results for certain compounds are shown in Table 1. Results are expressed as micrometers squared times $10^{-3}$.

TABLE 1

| INHIBITION OF THE INVASIVE ACTIVITY OF HT 1080 CELLS | | | | |
|---|---|---|---|---|
| | Concentration ($\mu$M) | | | |
| COMPOUND | 0 | 1 | 10 | 50 |
| EXAMPLE 4 | 108.8 | 88.5 | 56.0 | 16.0 |
| EXAMPLE 9 | 108.8 | — | 71.78 | 52.16 |
| EXAMPLE 11 | 108.8 | — | 69.15 | 56.9 |

The following non limiting examples further illustrate details for the preparation of compounds used in practicing the present invention. Those skilled in the art will readily understand and appreciate that known variations of the conditions and procedures in the following preparative methods can be utilized. All temperatures are degrees Celsius unless otherwise noted. Melting points were determined on a Thomas Hoover melting point apparatus and are uncorrected.

EXAMPLE 1

Preparation of
3,5-bis(1,1-dimethylethyl)-4-hydroxyphenylthiocyanate

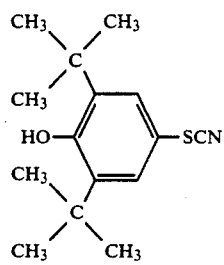

To a three-necked, round bottom 5 L flask, equipped with a mechanical stirrer, gas inlet, thermometer and gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° .C, chlorine gas was slowly bubbled through the mixture for about 1 hour whereupon the reaction mixture was a heterogeneous yellow color. Ammonia was then bubbled h the reaction for about 1½ hours, maintaining the reaction mixture at a temperature of between 0° to 10° C. The reaction was stirred for an additional hour at 0° C., poured into 2 L of cold distilled water and refrigerated overnight. The aqueous phase was decanted and the solid taken up in methanol, precipitated from water, filtered and dried for 2 days over phosphorous pentoxide. The resulting gummy yellow solid was recrystallized from pentane and dried in vacuo to yield the product as a white powder, m.p. 61.5°–63° C. Analysis calc. for $C_{15}H_{21}NSO$: Theory: C, 68.40; H, 8.03; N, 5.32; S, 12.17. Found: C, 68.85; H, 8.05; N, 5.29; S, 12.12.

EXAMPLE 2

Preparation of
2,6-bis(1,1-dimethylethyl)-4-mercaptophenol

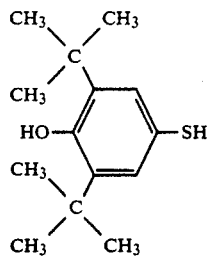

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product

EXAMPLE 3

Preparation of
N-methyl-N-[2-(2-pyridinyl)ethyl]-2-propenamide

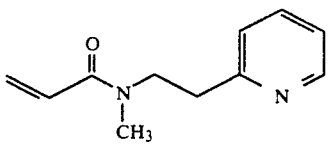

Acryloyl chloride (4.52 g, 0.05 mole) was added dropwise to a stirring solution of triethylamine (30 ml) and 2-β-methylaminoethyl)pyridine (6.81 g, 0.05 mole) in ethyl ether (500 ml). After stirring overnight at room temperature, the white solid was removed by filtration and washed well with ethyl ether. The organic phases were combined, dried over sodium sulfate, filtered then concentrated to dryness to give an orange oil. The structure was confirmed by NMR.

EXAMPLE 4

Preparation of
3-[[3,5-bis(1,1-dimethylethyl)-4-hydroxyphenyl]thio]-
N-methyl-N-[2-(2-pyridinyl)ethyl]propanamide

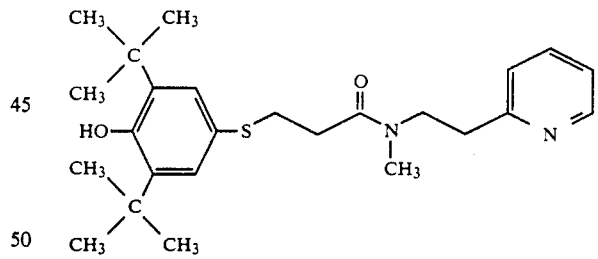

N-methyl-N-[2-(2-pyridinyl)ethyl]-2-propenamide (0.95 g, 0.005 mole) was dissolved in methanol (200 ml) containing 2,6-bis(1,1-dimethylethyl)-4-mercaptophenol (1.19 g, 0.005 mole). After addition of triethylamine (0.5 ml), the solution was stirred at room temperature overnight. The solvent was removed by a nitrogen stream to give a residue which was purified by chromatography on silica to give the title compound, m.p. ca. 82°–84° C. Anal. calcd. for $C_{25}H_{36}N_2O_2S$(428.62): Calc.: C, 70.05; H, 8.47; N, 6.54; S, 7.47. Found: C, 70.45; H, 8.50; N, 6.60; S, 7.55.

EXAMPLE 5

Preparation of
3-[[3,5-bis(1,1-dimethylethyl)-4-hydroxyphenyl]thio]-
N-methyl-N-[2-(2-pyridinyl)ethyl]propanamide
monohydrochloride

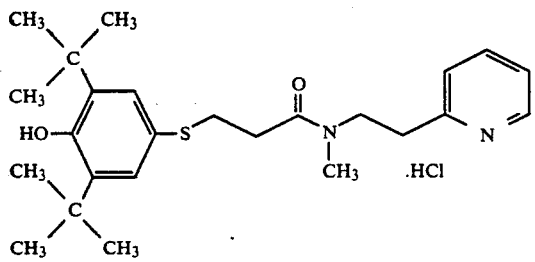

The title compound of Example 4, (2.0 g) was dissolved in ethyl ether (400 ml). With rapid stirring, a saturated solution of hydrogen chloride in isopropyl alcohol was added dropwise until no further precipitation occurred. The oily material was stirred for 20 hours. The ethyl ether was decanted and the residue crystallized from ethyl acetate/ethyl ether to give the title compound (700 mg), m.p. ca. 153°–156° C. Analysis calc for $C_{25}H_{37}N_2SOCl(465.09)$: Calc.: C, 64.56; H, 8.02; N, 6.02; Cl, 7.62; S, 6.89. Found: C, 64.30; H, 7.88; N, 6.00; Cl, 7.79; S, 6.91.

EXAMPLE 6

Preparation of
N-ethyl-N-(4-pyridinylmethyl)-2-propenamide

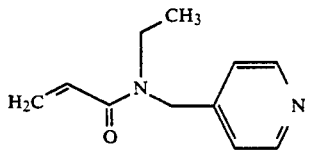

Following the method of Example 3, 4-picolyl ethylamine (4.27 g, 0.035 mole) was reacted with acryloyl chloride (3.15 g, 0.035 mole) and triethylamine (21 ml) and purified by chromatography on silica. Analysis calc. for $C_8H_{12}N_2(136.20)$: Calc.: C, 69.44; H, 7.92; N, 14.72. Found: C, 69.26; H, 7.56; N, 14.59.

EXAMPLE 7

Preparation of
3-[[3,5-bis(1,1-dimethylethyl)-4-hydroxyphenyl]thio]-
N-ethyl-N-(4-pyridinylmethyl)propanamide

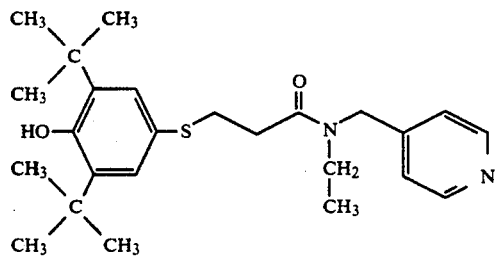

The title compound was prepared according to the method of Example 4 from N-ethyl-N-(4-pyridinylmethyl)-2-propenamide (1.5 g, 0.00788 mole,), 2,6-bis(1,1-dimethylethyl)-4-mercaptophenol (2.06 g, 0.00867 mole,) and triethylamine (1 ml) to provide 3.0g of product, m.p. ca. 121°–123° C. Analysis calc. for $C_{25}H_{36}N_2O_2S(428.63)$: Calc.: C, 70.05; H, 8.47; N, 6.54; S, 7.48. Found: C, 70.23; H, 8.55; N, 6.34; S, 7.55.

EXAMPLE 8

Preparation of
N-methyl-N-[(2-methyl-6-pyridinyl)methyl]-2-propenamide

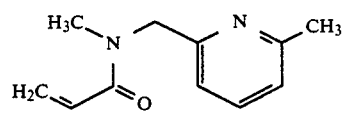

The title compound was prepared according to the method of Example 6 from 6-methyl-2-picolylmethylamine (4.27 g, 0.035 mole), acryloyl chloride (3.15 g, 0.035 mole) and triethylamine (21 ml) in methylene chloride. Analysis calc. for $C_{11}H_{14}N_2O(190.24)$: Calc.: C, 69.44; H, 7.42; N, 14.72. Found: C, 69.41; H, 7.53; N, 14.68.

EXAMPLE 9

Preparation of
3-[[3,5-bis(1,1-dimethylethyl)-4-hydroxyphenyl]thio]-
N-methyl
N-[(2-methyl-6-pyridinyl)methyl]propanamide

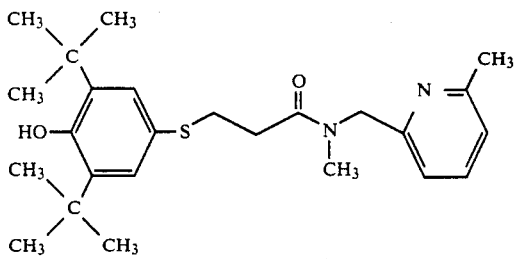

The title compound was prepared according to the method of Example 4 from the amide of Example 8 (1.9 g, 0.01 mole), the thiol of Example 4 (2.38 g, 0.01 mole) and triethylamine (1 ml) in methanol to provide 3.95 g of product. Analysis calc. for $C_{25}H_{36}N_2O_2S(428.63)$: Calc.: C, 70.05; H, 8.47; N, 6.54; S, 7.48. Found: C, 69.80; H, 8.59; N, 6.32; S, 7.57.

EXAMPLE 10

Preparation of
N-methyl-N-[2-(4-pyridinyl)ethyl]-2-propenamide

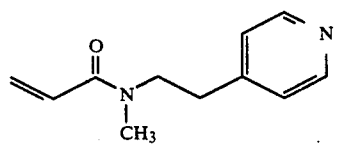

The title compound was prepared according to the method of Example 3 from 4-[β-(methylamino)ethyl]-pyridine (4.76 g, 0.035 mole), acryloyl chloride (3.15 g, 0.035 mole) and triethylamine (21 ml) to yield 3.4 g of product, m.p. ca. 129°–132° C. Analysis calc. for $C_{11}H_{14}N_2O(190.24)$: Calc.: C, 69.45; H, 7.42; N, 14.72. Found: C, 69.79; H, 7.62; N, 14.20.

EXAMPLE 11

Preparation of 3-[[3,5-bis(1,1-dimethylethyl)-4-hydroxyphenyl]thio]-N-methyl-N-[2-(4-pyridinyl)ethyl]propanamide

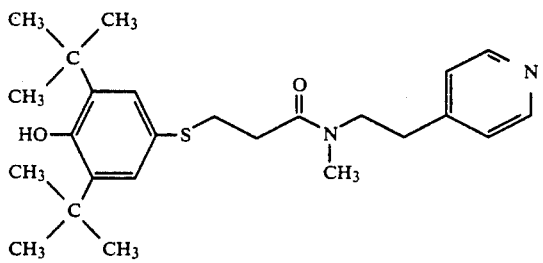

The title compound was prepared according to the method of Example 4 from the thiol of Example 2 (2.61 g, 0.011), the amide of Example 10 (1.9 g, 0.010 mole) and triethylamine (1 ml) to yield 3.4 g of product, m.p. ca. 129°–131.5° C. Analysis calcd. for $C_{25}H_{36}N_2O_2S(428.63)$: Calcd.: C, 70.05; H, 8.47; N, 6.53; S, 7.48. Found: C, 70.15; H, 8.58; N, 6.47; S, 7.71.

EXAMPLE 12

Preparation 3,5-dichloro-4-hydroxyphenyl thiocyanate

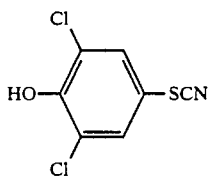

2,6-Dichlorophenol (100 g, 0.613 mole) and ammonium thiocyanate (102.73 g, 1.350 mole) were mixed in methanol and the solution cooled to 0° C. Chlorine gas was bubbled through the reaction, maintaining the temperature below 10° C. The solution turned a pale yellow color. The reaction was stirred for a total of 3 hours until acidic, at which time ammonia gas was bubbled through and the solution stirred for an additional three hours at 0° to 10° C. The reaction was poured into iced distilled water, and filtered, yielding approximately 20 g of a yellow solid which was dried overnight in vacuo. The filtrate was extracted with ethyl acetate, dried over magnesium sulfate and stripped to yield approximately 100 g of crude product. Following purification by chromatography, the material was taken up to 1 liter of toluene, charcoal added, filtered and recrystallized from hexane to yield 55.03 g of product as a yellow solid. The structure was confirmed by NMR.

EXAMPLE 13

Preparation of 2,6-dichloro-4-mercaptophenol

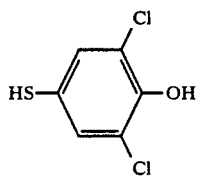

The title compound of Example 12 (55.03 g, 0.25 mole) was dissolved in 300 ml of acetone. Water (9 ml), was added and the solution cooled to 0° C. Triethylphosphine (36.9 ml, 0.250 mole) was added dropwise over a period of 65 minutes, maintaining the temperature at 0° C. The reaction was allowed to warm to room temperature, stirred for 1½ hours, the solvent was removed and the product purified by chromatography and recrystallized from hexane to give the title compound. Analysis Calcd. for $C_6H_4OCl_2S(195.08)$: Calcd.: C, 36.94; H, 2.07; Cl, 36.35; S, 16.44. Found: C, 36.96; H, 2.06; Cl, 36.31; S, 16.56.

EXAMPLE 14

Preparation of 3-[(3,5-dichloro-4-hydroxyphenyl)thio]-N-methyl-N-[2-(2-pyridinyl)ethyl]propanamide

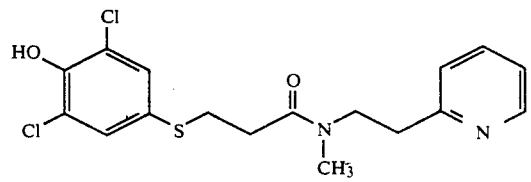

The title compound was prepared according to the method of Example 4, from N-methyl-N-[2-(2-pyridinyl)-ethyl]-2-propenamide (2.5 g. 0.013 mole), 2,6 dichloro-4-mercaptophenol (2.56 g, 0.013 mole) and triethylamine (5 ml), m.p. about 120°–123° C. Analysis calc. for $C_{17}H_{18}N_2O_2Cl_2S$ (385.31): Calc.: C, 52.97; H, 4.71; N, 7.27; Cl, 18.40; S, 8.32. Found: C, 53.18; H, 4.89; N, 7 34; Cl, 18.59; S, 8 05.

EXAMPLE 15

Preparation of 2'-hydroxyl[1,1':3',1''-terphenyl]-5'-yl thiocyanate

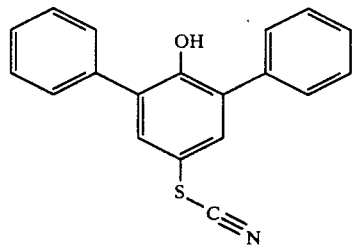

2,6-Diphenylphenol (100.0 g, 0.406 mole) and ammonium thiocyanate (67.99 g, 0.893 mole) were suspended in methanol (150 ml) in a three necked round bottom flask equipped with magnetic stirrer, thermometer and bubbler. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then poured into iced distilled water and allowed to stand for 12 hours in the refrigerator. After filtering, the solid was dried in vacuo at 45° C. for 12 hours. The title compound was purified by chromatography and recrystallized from hexane, m.p. about 104°–106.5° C. Analysis calc. for $C_{19}H_{13}OSN(303.39)$: Calc.: C, 75.22; H, 4.32; N, 4.62; S, 10.57. Found: C, 75 12; H, 4.49; N, 4.65; S, 10.41.

EXAMPLE 16

Preparation of 5'-mercapto[1,1':3',1''-terphenyl]-2'-ol

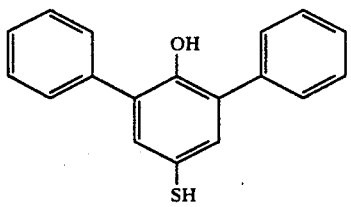

The title compound of Example 15 (32.2 g, 0.106 mole) and water (1.9 ml) were dissolved in acetone (150 ml) with stirring and cooled to −5° C. Triethylphosphine (15.7 ml, 0.106 mole) was added dropwise over a period of 40 minutes. The reaction was stirred at 0° C. for 1 hour and then at room temperature for 2 hours. The solvent was evaporated and the product isolated by chromatography on silica. Analysis Calcd. for $C_{18}H_{14}OS$ (278.31): Calcd.: C, 77.67; H, 5.07; S, 11.52. Found: C, 77.80; H, 5.19; S, 11.68.

EXAMPLE 17

Preparation of 3-[(2'-hydroxy[1,1':3',1''-terphenyl]-5'-yl)-thio]-N-methyl-N-[2-(2-pyridin-yl)ethyl]propanamide

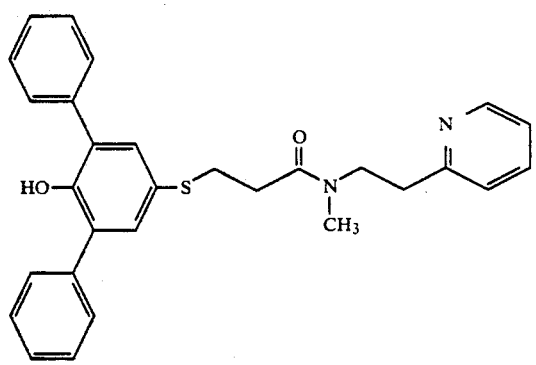

The title compound was prepared according to the method of Example 4 from the thiol of Example 16(2.78 g, 0.01 mole), N-methyl-N-[2-(2-pyridinyl)ethyl]-2-propenamide (1.90 g, 0.01 mold) and triethylamine (1.2 ml). Analysis calc. for $C_{29}H_{28}O_2N_2S$ (468.54): Calc.: C, 74.32; H, 6.02; N, 5.98. Found: C, 73.93; H, 6.04; N, 6.16.

EXAMPLE 18

Preparation of 4-[[3,5-bis(1,1-dimethylethyl)-4-hydroxyphenyl]thio]-butanoic acid

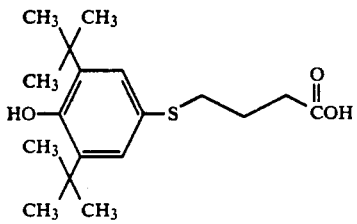

Potassium hydroxide flakes (2.52 g, 0.045 mole) were added to a clear solution of 2,6-bis(1,1-dimethylethyl)-4-mercaptophenol (3.57 g, 0.015 mole) and ethyl 4-bromo butyrate (3.23 g, 0.0165 mole) in acetone (10 ml). Water (20 ml) was added and the solution stirred for 1.5 hours, the solvent removed on a rotary evaporator and water (50 ml) added. The organic layer was extracted with ethyl ether (3×75 ml). The aqueous layer was acidified with concentrated hydrochloric acid, extracted with ethyl ether (2×50 ml), washed with water (50 ml), dried over sodium sulfate, filtered and the solvents removed, leaving an oil, which was purified by chromatography on silica, recrystallized from ethyl ether/Skellysolve B, filtered and the product dried in vacuo at room temperature for 12 hours, m.p. ca. 112°–113.5° C. Analysis calc. for $C_{18}H_{28}O_3S$(324.48): Calc.: C, 66.63; H, 8.70; S, 9.88. Found: C, 66.71; H, 8.74; S, 9.57.

EXAMPLE 19

Preparation of 4-[4-[3,5-bis(1,1-dimethylethyl)-4-hydroxyphenyl]thio]-N-methyl-N-[2-(2-pyridinyl)ethyl]butanamide

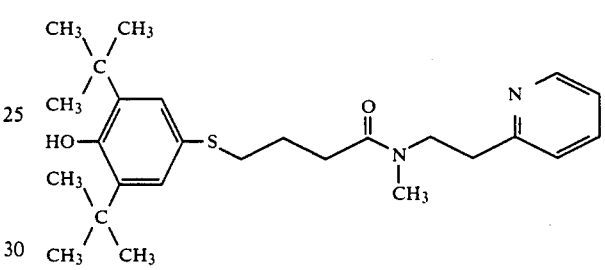

The title compound of Example 18 is dissolved in benzene and the solution cooled to about 5° C. in an ice bath. A solution of oxalyl chloride in benzene is added dropwise over a period of about 5 minutes. The ice bath is removed and the solution is allowed to warm to room temperature and is stirred for about 5 hours. The benzene is evaporated and fresh benzene is added. Triethylamine and 2-(β-methylaminoethyl)pyridine are added and the solution is stirred overnight. The benzene is evaporated on a rotary evaporator and the product is purified by chromatography on silica.

EXAMPLES 20–22

By replacing 2,6-bis-(1,1-dimethylethyl)-4-mercaptophenol with 2,6-dichloro-4-mercaptophenol in the procedures of Examples 7, 9, and 11, the following compounds are obtained.

Example 20. 3-[(3,5-dichloro-4-hydroxyphenyl)thio]-N-ethyl-N-(4-pyridinylmethyl)propanamide.

Example 21. 3-[(3,5-dichloro-4-hydroxyphenyl)thio]-N-methyl-N-[(2-methyl-6-pyridinyl)methyl]propanamide.

Example 22. 3-[(3,5-dichloro-4-hydroxyphenyl)thio]-N-methyl -N-[2-(4-pyridinyl)ethyl]propanamide.

EXAMPLES 23–25

By replacing 2,6-bis(1,1-dimethylethyl)-4-mercaptophenol with 5'-mercapto[1,1':3',1''-terphenyl]-2'-ol in the procedures of Examples 7, 9 and 11, the following compounds are obtained.

Example 23. 3-[(2'-hydroxy[1,1':3',1''-terphenyl]-5'-yl) thio]-N-ethyl-N-(4-pyridinylmethyl)propanamide.

Example 24. 3-[(2'-hydroxy[1,1':3',1''-terphenyl]-5'-yl) thio]-N-methyl-N-[(2-methyl-6-pyridinyl)methyl]propanamide.

Example 25. 3-[(2'-hydroxy[1,1':3',1''-terphenyl]-5'-yl)thio]-N-methyl-N-[2-(4-pyridinyl)ethyl]propanamide.

Examples 26–32

By substituting the appropriate alkylpyridyl amide for the starting amides of Examples 4, 7, 9, 11, etc., the following representative products are obtained.

Example 26. 4-[(2'-hydroxy[1,1':3',1''-terphenyl]-5'yl)thio]-N-methyl N [2-(2-pyridinyl)ethyl]butanamide.

Example 27. 2-[(3,5-dichloro-4-hydroxyphenyl)thio]-N-ethyl-N-(4-pyridinylmethyl)acetamide.

Example 28. 2-[(3,5-dichloro-4-hydroxyphenyl)thio]-N-methyl-N- [(2-methyl-6-pyridinyl)methyl]ethanamide.

Example 29. 3-[(3,5-dichloro-4-hydroxyphenyl)thio]-N-methyl-N- [2-(2-pyridinyl)ethyl]iso-propanamide.

Example 30. 4-[(3,5-bis(1,1-dimethylethyl)-4--hydroxyphenyl]thio]-N-methyl-N-[2-(2-pyridinyl)ethyl]2,2-dimethylbutanamide.

Example 31. 2-[(2'-hydroxy[1,1':3',1''-terphenyl]-5'-yl)thio]-N-methyl-N-[2-(4-pyridinyl)ethyl]pentanamide.

Example 32. 2 [-(2'-hydroxy[1,1':3',1''-terphenyl]-5'-yl)thio]-N-methyl-N-[2-(4-pyridinyl)ethyl]hexanamide.

The active agents of this invention can be administered to animals, including humans and other mammals, as pure compounds. Thus, the word animals is used in its broadest sense. However, it is advisable to first combine one or more of the active compounds with one or more suitable pharmaceutically acceptable carriers or diluents to attain a satisfactory size to dosage relationship and thereby obtain a pharmaceutical composition.

Pharmaceutical carriers which are liquid or solid can be employed. Solid carriers such as starch, sugars, talc and the like can be used to form powders which may be used for direct administration or to fill gelatin capsules. Suitable lubricants such as magnesium stearate, stearic acid, as well as binders and disintegrating agents may be included to form tablets. Additionally, flavoring and sweetening agents may be added.

Unit dosage forms such as tablets and capsules can contain any suitable, predetermined, therapeutically effective amount of one or more active agents and a pharmaceutically acceptable carrier or diluent. Generally speaking, solid oral unit dosage forms of a compound of this invention will contain from 1.75 to 750 mg per tablet of drug.

The compounds of this invention exhibit both oral and parenteral activity and accordingly can be formulated in dosage forms for either oral or parenteral administration.

Solid oral dosage forms include capsules, tablets, pills, powders, granules and the like.

Liquid dosage forms for oral administration include emulsions, suspensions, solutions, syrups and the like containing diluents commonly used in the art such as water. Besides inert diluents, such preparations can also include adjuvants such as wetting agents, emulsifying and suspending agents, and sweetening, flavoring and perfuming agents.

Preparations for parenteral administration include sterile aqueous or non aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The compounds used in this invention may also be formulated for topical or transdermal application using carriers which are well known in the art, as well as in aerosols or sprays for nasal administration.

The amount of active ingredient administered may be varied; however, it is necessary that the amount of active ingredient be such that a suitable dosage is given. The selected dosage depends upon the desired therapeutic effect, the route of administration and the duration of treatment. Generally speaking, oral dosages of from 0.1 to 200 mg/kg, and preferably from 0.5 to 50 mg/kg of body weight daily are administered to patients in need of such treatment, preferably in divided dosages, e.g. three to four times daily. Alternatively, sustained release formulations can be prepared and used.

A typical tablet of this invention can have the following composition:

| Ingredient | Mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

It will be understood by those skilled in the art that the above examples are illustrative, not exhaustive, and that modifications may be made without departing from the spirit of the invention and the scope of the claims.

What is claimed is:

1. A method of inhibiting invasive activity and related metastasis of tumor cells in a mammal comprising administering an amount of a compound of the formula

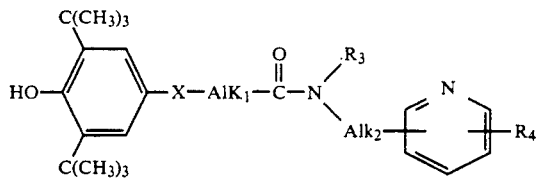

wherein X is thio or sulfinyl; $Alk_1$ is straight or branched chain lower alkylene of 1 to 6 carbon atoms; $R^3$ is hydrogen or lower alkyl; $Alk_2$ is straight or branched chain alkylene of 1 to 4 carbon atoms; and $R_4$ is selected from the group consisting of hydrogen, halo, hydroxy lower alkyl, and lower alkoxy; or a pharmaceutically acceptable salt thereof, which is effective to inhibit tumor cell invasive activity and related metastasis to a mammal having tumor cells sensitive to said compound.

2. A method according to claim 1 wherein $Alk_1$ is ethylene.

3. A method according to claim 1 wherein X is thio.

4. A method according to claim 1 wherein X is sulfinyl.

5. A method according to claim 1 wherein said compound is, 3-[[3,5-bis(1,1-dimethylethyl)-4-hydroxyphenyl]thio]-N methyl-N-[2-(2-pyridinyl)ethyl]propanamide or a pharmaceutically acceptable acid addition salt thereof.

6. A method according to claim 1 wherein said compound is, 3-[[3,5-bis(1,1-dimethylethyl)-4-hydroxyphenyl]thio]-N-methyl-N-[2-(2-pyridinyl)ethyl]-propanamide monohydrochloride.

7. A method according to claim 1 wherein said compound is, 3-[[3,5-bis(1,1-dimethylethyl)-4-hydroxyphenyl] thio]-N-ethyl-N-(4-pyridinylmethyl)-propanamide or a pharmaceutically acceptable acid addition salt thereof.

8. A method according to claim 1 wherein said compound is, 3-[[3,5-bis(1,1-dimethylethyl)-4-hydroxyphenyl]thio]-N-methyl-N-](2-methyl-6-pyridinyl)-methyl] propanamide or a pharmaceutically acceptable acid addition salt thereof.

9. A method according to claim 1 wherein said compound is, 3-[[3,5-bis(1,1-dimethylethyl)-4-hydroxyphenyl]thio]-N-methyl-N-[(2-(4-pyridinyl)ethyl]-propanamide or a pharmaceutically acceptable acid addition salt thereof.

* * * * *

UNITED STATES PATENT AND TRADEMARK OFFICE
CERTIFICATE OF CORRECTION

PATENT NO. : 5,030,642                    Page 1 of 2
DATED     : Jul. 9, 1991
INVENTOR(S) : Fuller et al.

It is certified that error appears in the above-identified patent and that said Letters Patent is hereby corrected as shown below:

On Title page
In the ABSTRACT, reading "an acrylaminoalkyl-" should read -- an acylaminoalkyl- --.

Column 7, line 20, reading "was added 2,6di-" should read -- was added 2,6-di- --.

Column 7, line 29, reading "bubbled h the" should read -- bubbled through the --.

Column 9, line 41, reading "Example 3, 4-picolyl ethyl" should read -- Example 3, 4-picolyl-ethyl --.

Column 10, line 28, reading "N-methyl" should read -- N-methyl- --.

Column 11, line 19, reading "g, 0.011)," should read -- g, 0.011 mole), --.

Column 12, line 67, reading "Found: C, 75 12;" should read -- Found: C, 75.12; --.

Column 13, line 48, reading "(1.90 g, 0.01 mold)" should read -- (1.90 g, 0.01 mole) --.

UNITED STATES PATENT AND TRADEMARK OFFICE
CERTIFICATE OF CORRECTION

PATENT NO. : 5,030,642

DATED : Jul. 9, 1991

INVENTOR(S) : Fuller et al.

It is certified that error appears in the above-identified patent and that said Letters Patent is hereby corrected as shown below:

Column 15, line 10, reading "N-methyl N [2-" should read -- N-methyl-N-[2- --.

Signed and Sealed this

Twenty-ninth Day of December, 1992

Attest:

DOUGLAS B. COMER

Attesting Officer

Acting Commissioner of Patents and Trademarks